United States Patent [19]

Arakawa

[11] Patent Number: 4,617,915

[45] Date of Patent: Oct. 21, 1986

[54] CONSTRUCTION OF MANUAL CONTROL SECTION OF ENDOSCOPE

[75] Inventor: Satoshi Arakawa, Oomiya, Japan

[73] Assignee: Fuji Photo Optical Co., Ltd., Japan

[21] Appl. No.: 726,398

[22] Filed: Apr. 23, 1985

[30] Foreign Application Priority Data

Apr. 24, 1984 [JP] Japan ............................. 59-60513[U]
Apr. 24, 1984 [JP] Japan ............................. 59-60514[U]
Apr. 24, 1984 [JP] Japan ............................. 59-60515[U]
Apr. 24, 1984 [JP] Japan ............................. 59-60516[U]

[51] Int. Cl.⁴ ............................................. A61B 1/00
[52] U.S. Cl. ........................................................ 128/4
[58] Field of Search ............................. 128/3, 4, 5, 6, 7

[56] References Cited

U.S. PATENT DOCUMENTS 3,091,235 5/1963 Richards ................................. 128/6
4,290,421 9/1981 Siegmund ............................... 128/6
4,539,586 9/1985 Danna et al. ........................ 128/6 X

FOREIGN PATENT DOCUMENTS 428589 12/1947 Italy ......................................... 128/6

Primary Examiner—William H. Grieb
Attorney, Agent, or Firm—Parkhurst & Oliff

[57] ABSTRACT

An endoscope includes in a viewing head of its insertable section into a cavity of a living body an image sensor for generating a video signal which in turn is transmitted to a television display to be visualized thereon as a television picture. A manual control section of the endoscope according to the present invention comprises a connector section connected to the rear end of the insertable section on one and same axial line and a grip section. The center axis of which is inclined at an angle $\theta$ ($90° < \theta < 180°$) to the center axis of the connector section, being grasped at least with a third finger and a little finger, the connector section and the grip section forming a generally pistol shape. As the result, the manual control section is formed into a generally pistol shape, whereby control buttons for air and water supply and for suction can be provided at a position corresponding to a trigger portion, so that the handling of the control buttons can be facilitated. In consequence, even if the endoscope is used for a long period of time, the fatigue of the operator remains low.

4 Claims, 8 Drawing Figures

CONSTRUCTION OF MANUAL CONTROL SECTION OF ENDOSCOPE

BACKGROUND OF THE INVENTION

1. Field of the Invention

This invention relates to endoscopes, and more particularly to an endoscope wherein a solid state imaging device is provided at the forward end of an insertion portion and an object of interest is displayed for observation on a television screen or the like in response to a video signal obtained from the solid state imaging device.

2. Description of the Prior Art

Many conventional endoscopes have been constructed such that an objective lens and an eyepiece lens are disposed at opposite end portions of an image transmission optical fiber bundle, an image of an object of interest is focused at an end face of the optical fiber bundle through the objective lens, and the image which is transmitted through the optical fibers and appearing at the opposite end face is observed through the eyepiece lens. More specifically, as shown in FIG. 1, the conventional endoscope comprises a main body 10 of the control section, a flexible insertion section 12 connected to main body 10 of the control section, for insertion into a very deep portion of a living body or the like, and a cable 16 for connecting a control unit 14 incorporating various control mechanisms including a light source necessary for the endoscope to the main body 10 of the control section.

In fiberoptic endoscopes of this type, i.e., having an image transmission optical fiber bundle for transmitting an optical image of an object, which is observed through an eyepiece lens, the control section main body 10 comprises a grip section which can be necessarily grasped by one hand of an operator and an eyepiece section 17 disposed upwardly of this grip section and on the uppermost end of the control section 10. More specifically, as shown in FIG. 2, a grip section 10A connected to the rear end of an insertion section 12 is formed at the lower end portion of the main body 10 of control section, and further, an eyepiece section 17 including an eyepiece lens is provided on the top portion of the main body 10 of control section. Provided on the front face of the main body 10 of the control section are a first control button 18 for air and water supply and a second control button 20 for suction. With the above-described arrangement, in the control section of the endoscope, as shown in FIG. 2, the operator grasps the grip section 10A of the main body 10 of control section with a middle finger 22A, a third finger 22B and a little finger 22C of his left hand and operates the first or second control button 18 or 20 with an index finger 22D, while looking into the eyepiece section 17.

However, when using the conventional endoscope shown in FIGS. 1 and 2, to look into the eyepiece section 17, the operator is required to bring the main body 10 of control section close to his face by raising his arm, otherwise to bring his head close to the eyepiece section 17 by bending his body forward. Therefore, the operator will be obliged to assume an unnatural posture, undesirably resulting in that his arm, waist and the like become numb after a long periods of observation.

The cable 16 connecting the main body 10 of the control section to a control unit 14 is connected to an upper rear end portion of the main body 10 of the control section through a bendingly fastened portion 24. Because of this, a space necessarily must be provided between the main body 10 of control section and the front of the body of the operator, and, when the main body 10 of control section is rotated to apply a twist or the like to the insertion section 16, the arm of the operator and the main body 10 of control section may be twined around with the cable 16, thus interfering with operation.

Recently, on the other hand, there has been proposed an endoscope of the type, wherein a solid state imaging device such as a charge coupled device (CCD) or a metal oxide silicon (MOS) image sensor is provided at the forward end of the insertion section of the endoscope, and a video signal of the object of interest obtained from this solid state imaging device is displayed on a screen of a monitor television or the like, so that the object can be observed. Such devices eliminate the need for an eyepiece section 17 and reduce fatigue during operation for extended periods and result in easy handling. Furthermore, there is no need for the operator to look into the eyepiece section 17, thus enabling increased freedom of operator movement. Therefore, it is desirable to adopt a positional arrangement for connecting cable 16 and control section 10 to the control unit 14 which minimizes interference during use.

SUMMARY OF THE INVENTION

The present invention has been developed to obviate the above-described disadvantages of the prior art and has as its object the provision of an endoscope wherein operator fatigue is low in use for a long period of time, handling of the control buttons in the control section is easy, and the cable connecting the control section to the control unit does not interfere with the operator during operations.

To this end, the present invention relates to an endoscope having a solid state imaging device at a forward end of the insertion section which displays an object of interest for observation on a screen in response to an image signal from the object of interest obtained from the solid state imaging device manual control section of the endoscope in accordance with the invention; has a connector section connected to the rear end of the insertion section on one and the same axial line and a grip section, the center axis of which is inclined at an angle $\theta$ to the center axis of the connector section. The grip section is configured to be grasped at least with a third finger and a little finger, the connector section and the grip section forming a generally pistol shape, and the angle $\theta$ being set in between 90° and 180°.

BRIEF DESCRIPTION OF THE DRAWINGS

The exact nature of this invention, as well as other objects and advantages thereof, will be readily understood from consideration of the following specification relating to the accompanying drawings, in which like reference characters designate the same or similar parts throughout the figures thereof and wherein.

DETAILED DESCRIPTION OF THE INVENTION

Description will hereunder be given of the preferred embodiments of an endoscope according to the present invention with reference to the accompanying drawings.

Figure 1:
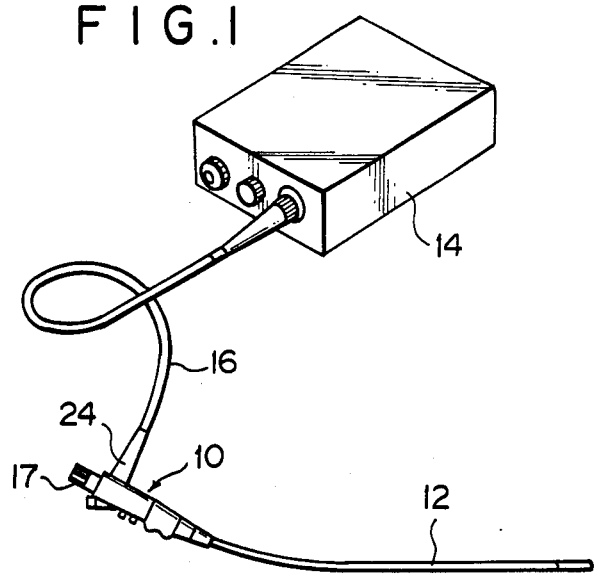
FIG. 1 is an explanatory view showing the general arrangement of the conventional endoscope.
Figure 2:
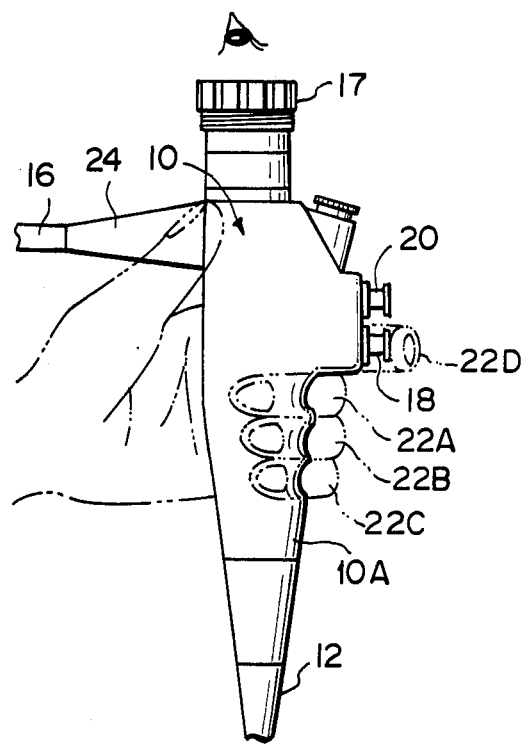
FIG. 2 is a front view showing the form of the control section of the conventional endoscope.
Figure 3:
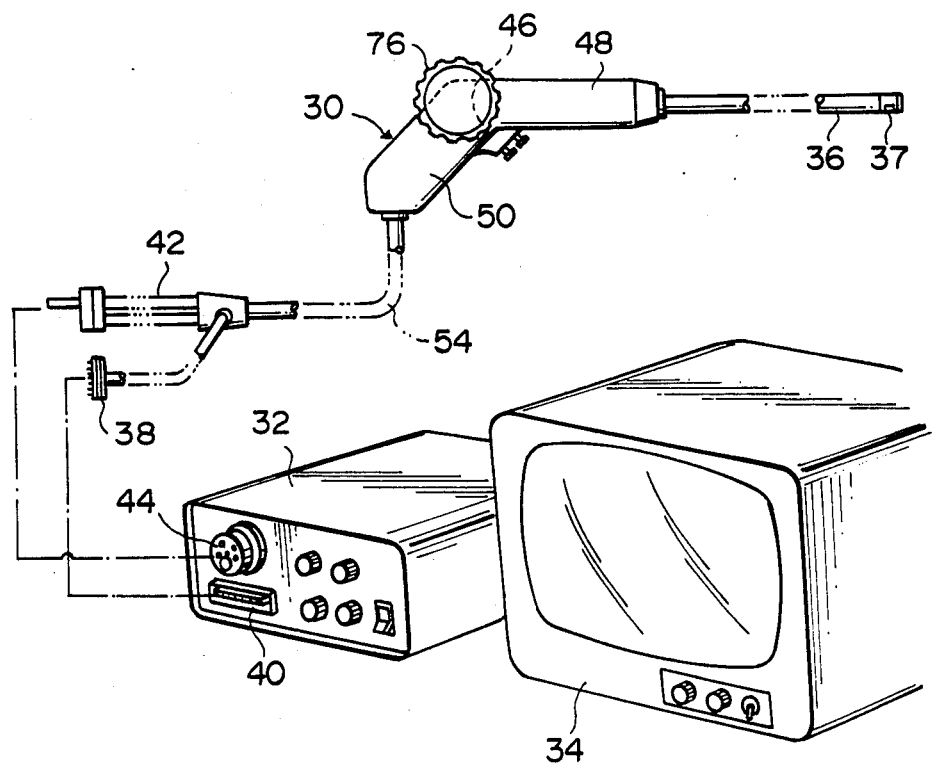
FIG. 3 is an explanatory view showing the general arrangement of the endoscope according to the present invention.

FIG. 3 shows the general arrangement of the endoscope according to the present invention. Designated at 30 is a control section, 32 a control unit and 34 a television monitor. A solid state imaging device 37 is provided at the forward end of an insertion section 36. The control unit 32 comprises a lamp for feeding light to a light guide, a process section for feeding a driving signal to the solid state imaging device 37 and processing a video signal obtained from the solid state imaging device, a power source and so on. The monitor television 34 displays an object of interest on a screen in response to a video signal obtained from the solid state imaging device 37 at the forward end of the insertion section 36 through the control unit 32. Additionally, a connector 38, to which is connected a lead wire of the solid state imaging device of the endoscope, is connected to a socket 40 of the control unit 32, and a plug 42 including a light guide and the like is connected to a socket 44.

Figure 4:
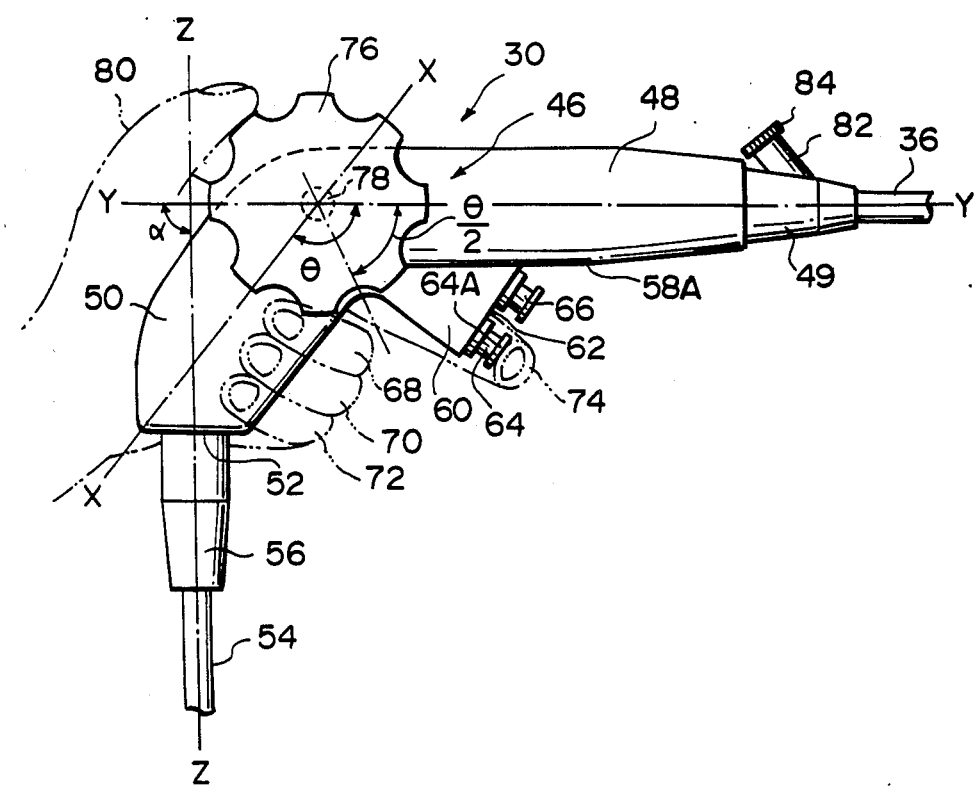
FIG. 4 is a front view showing the form of the manual control section in a first embodiment of the endoscope according to the present invention.

FIG. 4 shows the general arrangement of the control section 30 of the endoscope according to the present invention. The main body 46 of the control section 30 comprises a connector section 48 and a grip section 50. The center axis X—X of the grip section 50 is inclined at a predetermined angle $\theta$ to the center axis Y—Y of the connector section 48, and consequently, the main body 46 of control section is formed into a generally pistol shape. $\theta 0$ is preferably set in between 90° and 180°. The insertion section 36 is connected to the connector section 48 on the same axis of the center axis Y—Y of the connector section 48, and the rear end thereof is secured to the forward end portion 49 of the connector section 48. In this insertion section 36, there are arranged a light guide formed of an optical fiber bundle, a lead wire connected to the solid state imaging device 37, pipes for air and water supply and so on, which are not shown. On the other hand, provided on an undersurface 52 of the grip section 50 is a cable 54 connected to the control unit 32 cable 54 is suspended in a direction perpendicular to the axis Y—Y of the connector section (direction Z—Z) through the bendingly fastened portion 56.

Cable 54 is suspended downwardly from the arm of the operator grasping the grip section 50, so that the cable 54 does not contact the arm and body of the operator thereby interfering with the operator in use. Even when the position of the arm of the operator is varied or the posture of the main body 46 of the control section is changed, whereby the cable 54 is varied in the deflected condition, the cable 54 only changes its suspended length downwardly of the main body 46 of control section and does not twine around the arm of the operator and the main body 46 of control section. Because of this, in the case of the endoscope according to the present invention having the arrangement of the control section in which the eyepiece section is dispensed with the main body 46 of control section has substantial freedom of movement and posture without interference from cable 54. Thus a cable connecting arrangement giving rise to improved controllability during observation by use of the endoscope is obtained. Further, the arm and the like cannot become twined around with the cable 54, so that disconnections of the optical fibers in the cable 54 are much less frequent.

A pedestal 60 is formed at a position close to a corner portion of the undersurface 58A of the main body 46 of control section. Provided on the front face 62 of this pedestal 60 are a first control button 64 for air and water supply and a second control button 66 for suction. The first control button 64 is adapted to control a valve means, not shown. A finger receiving portion 64A is pressed in with the inner surface of a finger tip, and the air supply and water supply are changed over from each other depending on the extent of the depression of button 64. Similarly, the second control button 66 is pressed in with a finger tip to perform the sucking function.

These control buttons 64 and 66 are provided within a range of angle between 0° and $\theta/2$ as measured from the center axis Y—Y of the connector section 16 to a grip section 50 in the clockwise direction. In other words, when the main body 46 of control section is likened to a pistol, the control buttons 64 and 66 are located at a position corresponding to a trigger of the pistol. As a consequence, when the control buttons 64 and 66 are provided in this range, if the grip section 50 is grasped with a middle finger 68, a third finger 70 and a little finger 72 as shown in FIG. 4, then the control buttons 64 and 66 can be very easily operated by an index finger 74.

The main body 46 of control body is provided with an angle control knob 76 which is rotatable about a shaft 78. As shown, this angle control knob 76 is rotatably operated with a thumb 80 in the clockwise or counterclockwise direction, to rotatably drive a drum of an angle controlling mechanism, not shown, which is provided in the main body 46 of control section to linearly move a control wire inserted through the insertion section 36, so that the forward end portion of the insertion section 36 including the solid state imaging device 37 can be varied in its curved direction.

Further, a treating device opening 82 is provided at the forward end portion 49 of the connector section 48. This treating device opening 82 is used such that a cap on the opening is removed and a treating device, e.g., forceps, is inserted into or removed from the opening for insertion in the insertion section 36.

Description will hereunder be given of operation of embodiments of the endoscope according to the present invention with the above-described arrangement. Firstly, the operator grasps the grip section with his middle finger 68, third finger 70 and little finger 72. His upper arm and a lower arm, which are holding the grip section 50 are bent perpendicularly to each other, the upper arm is attached to his side of the chest and his wrist is stabilized. Subsequently, the operator, observing the television monitor 34, rotates the control knob 76 to direct the forward end portion of the insertion section toward the position of observation. Furthermore, the operator controls the control buttons 64 and 66 with his index finger 74 as necessary to perform the controls for water supply, or air supply and for suction. Further, as necessary, a forceps or the like is inserted through the treating device opening 82 to thereby collect a piece of flesh and the like from an affected portion.

In the above embodiment, description has been given of a case where the grip section 50 is grasped with the middle finger 68, third finger 70 and little finger 72 and the first and second buttons 64 and 66 are operated by the index finger 74, however, an arrangement may be adopted such that the grip section 50 is grasped with the third finger 70 and little finger 72, the second control button 66 is operated with the index finger 74 and the first control button 64 is operated by the middle finger 68.

Furthermore, in the above embodiment, the cable 54 is suspended from the undersurface 52 of the grip section 50, whereby no space is required between the control section 30 and the front of the body of the operator, so that the operator can stably hold the control section 30. When the control section 30 is rotated to apply a twist or the like to the insertion section 36, since the cable 54 is suspended from the undersurface 52 of the grip section 50 in a direction perpendicular to center axis Y—Y of the connector section 48, the arm, body and the like of the operator are not twined around with the cable 54, so that the operation of the control section 30 is facilitated.

Figure 5:
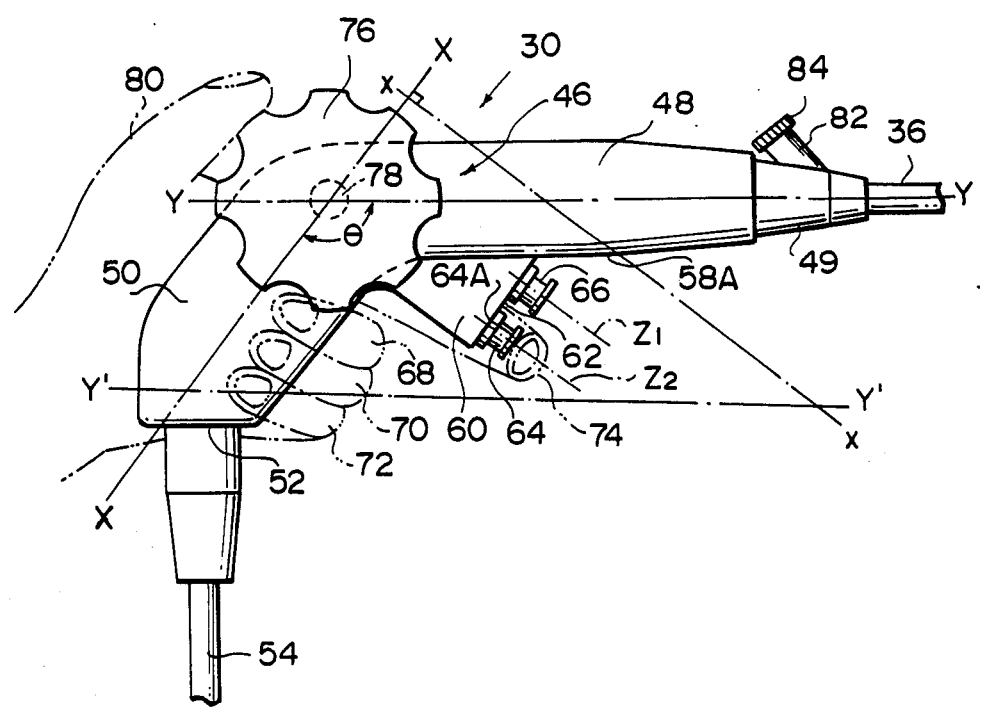
FIG. 5 is a front view showing the form of the manual control section in a second embodiment of the present invention.

FIG. 5 shows an arrangement of a second embodiment of the present invention, and, same reference numerals as shown in the first embodiment in FIG. 4 are used to designate same or similar parts, so that the detailed description thereof need not be repeated.

In the second embodiment, the center axes Z1 and Z2 of the press-in operations of the control buttons 64 and 66 are preset within a range of angle between a direction (a direction of Y'—Y') parallel to the center axis Y—Y of the connector section 48 and a direction (a direction of x—x) perpendicularly intersecting the center axis X—X of the grip section 50. In other words, when the main body 46 of control section is likened to a pistol, the direction of pressing in the control buttons 64 and 66 is a direction in which the trigger of the pistol is pulled, i.e. a direction in which joints of fingers naturally bend. Thus the center axes Z1 and Z2 of the press-in operations of the control buttons 64 and 66 are preset within the aforesaid angle range, such that, when the grip section 50 is grasped with the middle finger 68, third finger 70 and little finger 72, if the index finger 74 is applied to the finger receiving portions of the control buttons 64 and 66 and a press-in force is applied in the direction in which the joint of the finger naturally bends, then the direction of the press-in force agrees with the press-in directions of the control buttons 64 and 66, so that the operation is facilitated and operator fatigue is low.

Because the center of axes Z1 and Z2 of the press-in operations of the first and second control buttons 64 and 66 are present in the direction of bending about a joint of the index finger 74, operations can be performed naturally with no burden of being imposed on the index finger 74.

Figure 6:
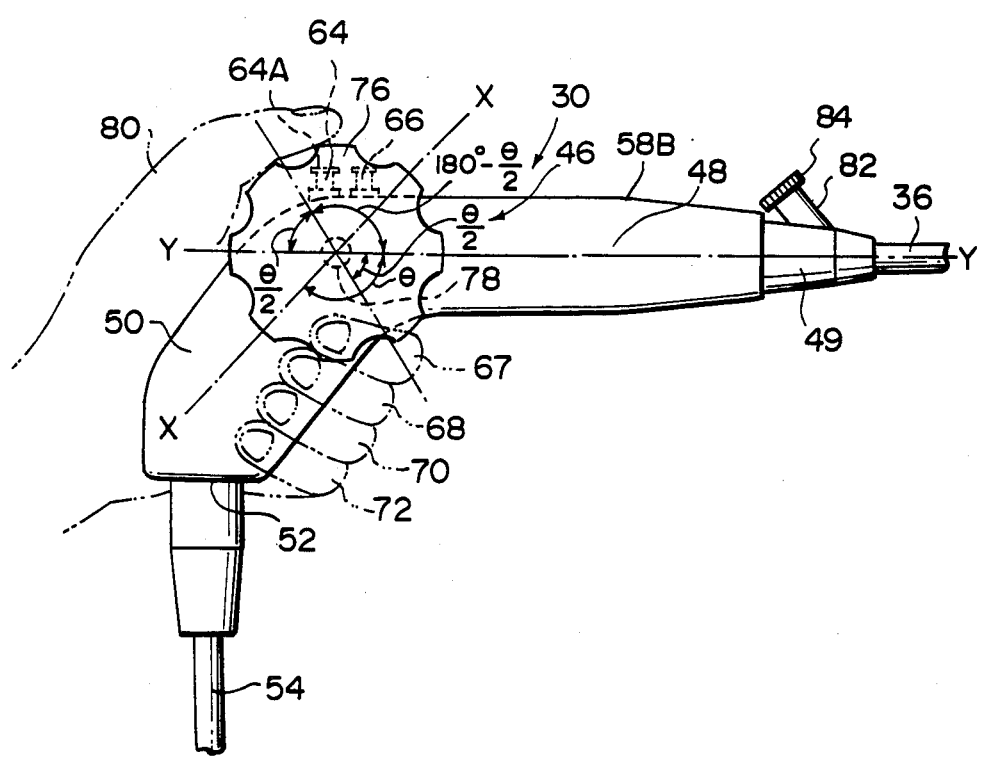
FIG. 6 is a front view showing the manual control section in a third embodiment of the present invention.

FIG. 6 shows an arrangement of a third embodiment of the present invention, and, same reference numerals as shown in the first and second embodiments are used to designate same or similar parts, so that the detailed description thereof need not be repeated.

The first control button 64 for air and water supply and the second control button 66 for suction are mounted in parallel on the top face 58B of the main body 46 of control section in the longitudinal direction and adjacent the rear end portion of the connector section 48. The first control button 64 is adapted to control a valve means, not shown. The finger receiving portion 64A is pressed in with the inner surface of a finger tip, and air supply and water supply are changed over from each other depending on the extent of depression of the button. Similarly, the second conrol button 66 is pressed in with a finger tip to perform the sucking function. These control buttons 64 and 66 are provided within a range of angle between 0° and 180°−θ/2 as measured from the center axis Y—Y to the rear portion of the connector section 48 (in the counter-clockwise direction from the center axis Y—Y). In other words, when the main body 46 of control section is likened to a pistol, the control buttons 64 and 66 are located at a position corresponding to a hammer of a pistol. When the control buttons 64 and 66 are provided in this range, if the grip section 50 is grasped with an index finger 67, middle finger 68, third finger 70 and little finger 72 as shown, then the control buttons 64 and 66 can be very easily operated with the thumb 80.

Figure 7:
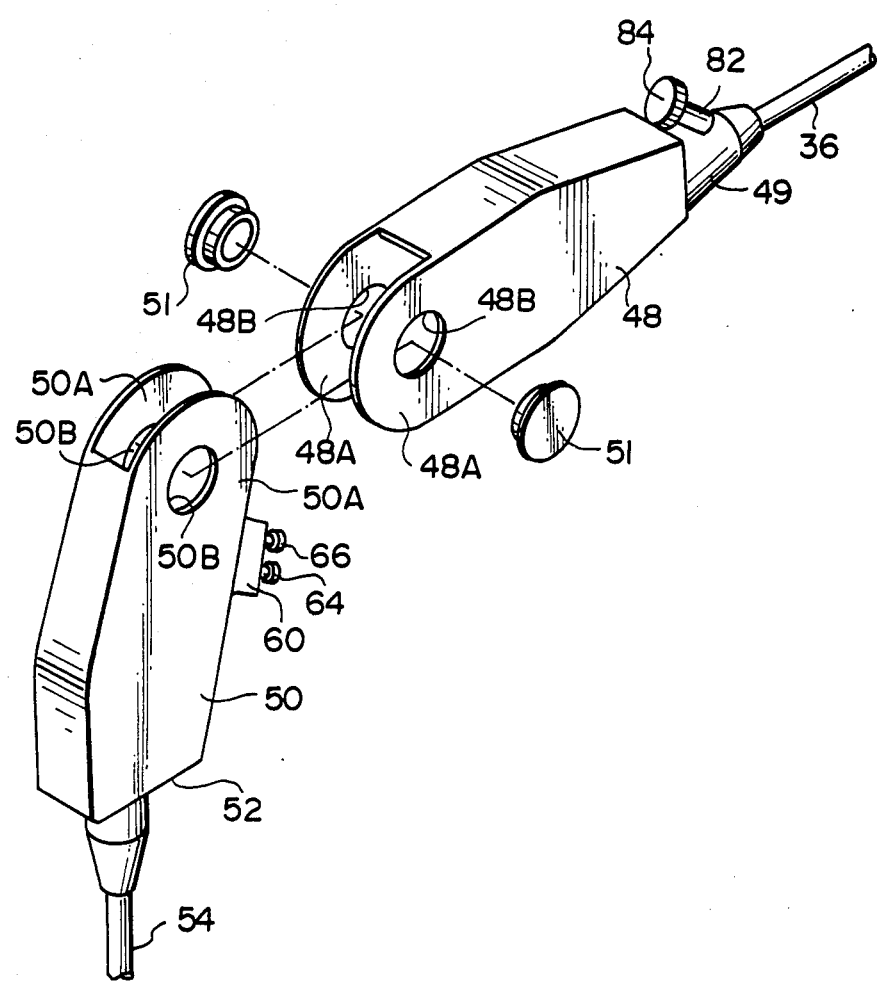
FIG. 7 is a front view showing the manual control section in a fourth embodiment of the present invention.

FIG. 7 shows an arrangement of a fourth embodiment of the present invention, and, same reference numerals as shown in the first, second and third embodiments are used to designate same or similar parts, so that the detailed description thereof need not be repeated.

The connector section 48 and the grip section 50 are provided in such a manner that the angle θ formed therebetween is adjustable. Namely, as shown in FIG. 7, both the connector section 48 and the grip section 50 are formed into generally rectangular parallelopipeds, and opposing rear end pieces 48A and 48A of the connector section 48 and opposing upper end portions 50A and 50A of the grip section 50 are pivotally mounted to each other through pins 51. The respective pins 51 are fastened to joint portions between shaft holes 48B and 48B formed in the opposing rear end pieces 48A and 48A of the connector section 48 and shaft holes 50B and 50B formed in the opposing upper end portions 50A and 50A of the grip section 50 through staking. With the above-described arrangement, a hollow space is formed in the pivotally mounted portion beween the connector section 48 and the grip section 50, so that insertion of the cable and the like is not hampered. The pivotally mounted portion includes a click mechanism using a pressing type turning ball, a latch mechanism and a well known rotation locking means using a screw, etc., all of which are not shown, so that the connector section 48 and the grip section 50 can be held at a desired crossing angle θ.

In handling the endoscope, the angle θ (Refer to FIG. 4) suitable for operation, formed by the center axis Y—Y of the connector section 48 and the center axis X—X of the grip section, must be determined in accordance with factors such as a stature of the operator. In this case, the angle θ formed by the connector sector 48 and the grip section 50 is rotated about the pins 51 to adjust to a predetermined angle at which the two center axes cross each other. Furthermore, the same thing is true of the case where the posture of the operator is changed.

In handling the endoscope as described above, there are also cases where the endoscope can be handled easier if the angle θ formed by the connector sector 48 and the grip section 50 is changed due to a position of the body of the patient, a position of an affected portion and the like. In this case, the angle θ can be adjusted as necessary.

Figure 8:
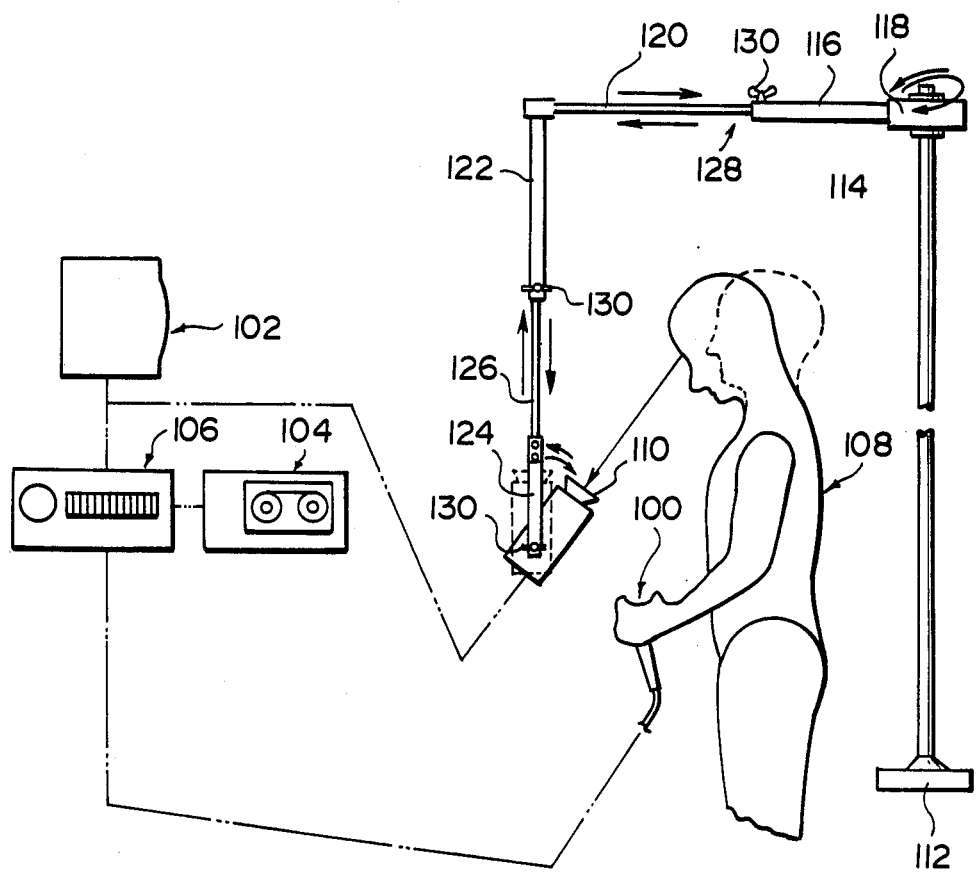
FIG. 8 is a front view showing the general arrangement of a fifth embodiment of the present invention.

FIG. 8 shows an arrangement of a fifth embodiment of the present invention. Referring to FIG. 8, designated at 100 is a manual control section of an endoscope, a relatively large display monitor 102, a video tape recorder 104 connected to a central control circuit 106 through a connecting cord schematically indicated by two-dot chain lines, and an operator 108 of the manual control section of the endoscope.

Denoted at 110 is a small-sized monitor exclusively used by the operator handling a manual control section 100 of the endoscope. This small-sized monitor 110 connected to the central control circuit 106 through a connecting cord schematically indicated by two-dot chain lines is supported by a small-sized monitor supporting member 128 comprising: a pedestal 112 for fixing this small-sized monitor 110 at a position close to the operator 108; a support pole 114 erected on the pedestal 112, and extendable and retractable in the vertical direction; a disc 118 with a hollow horizontal rod 116 fixably-rotatably mounted to the top end of the support pole 114; a horizontally extendable and retractable rod 120 being fixable, and insertable into and detachable from the hollow horizontal rod 116; a hollow suspended rod 122 fixed at the top end portion thereof to the free end of the rod 120; and a rod 126 being extendable and retractable in the suspended direction, provided with a bifurcated rod portion 124 for tiltably and fixably supporting the small-sized monitor 110 at the bottom end thereof. Additionally, designated at 130 are thumbscrews for fixing.

In the above embodiment, at the time of use, the small-sized monitor 110 is mounted to the bifurcated rod portion 124 for supporting the small-sized monitor. The small-sized monitor supporting member 128 should be fixed to a preset position close to the operator 108 by use of the pedestal 112, the support pole 114, the horizontally extandable and shrinkable rod 120, the rod 126, being extendable and retractable. Additionally, a picture plane of the small-sized monitor 110 can be tilted and fixed for easier observation by the operator, so that the operator can observe a clear image of the interior of a cavity in a living body, formed on a small-sized monitor 110 without raising or lowering his face and, even when the manual control section is located in his visual field.

What is claimed is:

1. An endoscope adapted to be held by an operator, comprising:

an insertion section having foreward and rearward ends, said foreward end including a solid state imaging device for sensing an image;

a connector section connected to said rearward end of said insertion section along a common axis with said rearward end;

a grip section connected to said connector section and arranged along an axis which is inclined with respect to said common axis of of said connector section and said insertion section by an angle θ, wherein θ is between 90° and 180°, said grip section and said connector section defining a pistol-shaped member having a rearward face, said rearward face being oriented closest to the operator when said endoscope is in use; and transmission means and push-button control means connected to said endoscope, said transmission means and push-button control means being located such that said rearward face of said endoscope is unobstructed.

2. An endoscope as set forth in claim 1, wherein said transmission means is a cable for carrying a video signal adapted for connection to a control unit, said cable being connected to said grip section and having an axis substantially perpendicular to said common axis of said connector section and said insertion section.

3. An endoscope as set forth in claim 1, wherein said push-button control means are located on an undersurface of the grip section.

4. An endoscope as set forth in claim 1, wherein said push-button control means are located on an upper surface of said connector section.

* * * * *